(12) United States Patent
Rokde

(10) Patent No.: US 11,944,346 B2
(45) Date of Patent: *Apr. 2, 2024

(54) OPTICAL TROCAR ASSEMBLY

(71) Applicant: Covidien LP, Mansfield, MA (US)

(72) Inventor: Rajat R. Rokde, Pune (IN)

(73) Assignee: Covidien LP, Mansfield, MA (US)

( * ) Notice: Subject to any disclaimer, the term of this patent is extended or adjusted under 35 U.S.C. 154(b) by 997 days.

This patent is subject to a terminal disclaimer.

(21) Appl. No.: 16/871,183

(22) Filed: May 11, 2020

(65) Prior Publication Data
US 2020/0268411 A1    Aug. 27, 2020

Related U.S. Application Data

(63) Continuation of application No. 16/167,625, filed on Oct. 23, 2018, now Pat. No. 10,736,659.

(51) Int. Cl.
*A61B 17/34* (2006.01)
*A61B 1/00* (2006.01)
*A61B 1/06* (2006.01)
*A61B 1/07* (2006.01)
*A61B 17/00* (2006.01)
(Continued)

(52) U.S. Cl.
CPC ...... *A61B 17/3423* (2013.01); *A61B 1/00032* (2013.01); *A61B 1/00167* (2013.01); *A61B 1/0607* (2013.01); *A61B 1/0684* (2013.01); *A61B 1/07* (2013.01); *A61B 17/0218* (2013.01); *A61B 17/3421* (2013.01); *A61B 2017/00477* (2013.01); *A61B 2017/00907* (2013.01); *A61B 2017/3454* (2013.01); *A61B 2090/309* (2016.02)

(58) Field of Classification Search
CPC ........ A61B 2090/306; A61B 2090/309; A61B 1/00165; A61B 1/167; A61B 2017/00477; A61B 2017/00907; A61B 2017/3454; A61B 17/0218; A61B 17/3421
See application file for complete search history.

(56) References Cited

U.S. PATENT DOCUMENTS 3,261,350 A    7/1966  Wallace
4,294,234 A   10/1981  Matsuo
(Continued)

FOREIGN PATENT DOCUMENTS

DE          19620887 A1    11/1997
DE       202008009527 U1    10/2008
(Continued)

OTHER PUBLICATIONS

European Search Report dated Jul. 25, 2012, corresponding to European Appliation No. 12163864; 7 pages.
(Continued)

*Primary Examiner* — Thomas M Sember
(74) *Attorney, Agent, or Firm* — Carter, DeLuca & Farrell LLP

(57) ABSTRACT

A cannula assembly configured to receive a surgical instrument therethrough includes an elongated body portion, a housing coupled to a proximal end portion of the elongated body portion, and an annular-shaped light member. The housing defines a longitudinally-extending channel therethrough dimensioned for passage of the surgical instrument. The light member is disposed within the housing and about the channel.

20 Claims, 2 Drawing Sheets

(51) Int. Cl.
*A61B 17/02* (2006.01)
*A61B 90/30* (2016.01)

(56) References Cited

U.S. PATENT DOCUMENTS

| | | | |
|---|---|---|---|
| 5,159,921 | A | 11/1992 | Hoover |
| 5,307,803 | A | 5/1994 | Matsuura et al. |
| 5,330,486 | A | 7/1994 | Wilk |
| 5,394,863 | A | 3/1995 | Sanford et al. |
| 5,419,312 | A | 5/1995 | Arenberg et al. |
| 5,656,013 | A | 8/1997 | Yoon |
| 5,666,222 | A | 9/1997 | Ning |
| 5,674,181 | A | 10/1997 | Iida |
| 5,685,823 | A | 11/1997 | Ito et al. |
| 5,725,477 | A | 3/1998 | Yasui et al. |
| 5,817,061 | A | 10/1998 | Goodwin et al. |
| 5,842,971 | A | 12/1998 | Yoon |
| 5,900,971 | A | 5/1999 | Ning |
| 5,960,145 | A | 9/1999 | Sanchez |
| 6,030,402 | A | 2/2000 | Thompson et al. |
| 6,440,061 | B1 | 8/2002 | Wenner et al. |
| 6,458,076 | B1 | 10/2002 | Pruitt |
| 6,554,793 | B1 | 4/2003 | Pauker et al. |
| 6,755,782 | B2 | 6/2004 | Ogawa |
| 6,840,909 | B2 | 1/2005 | Gatto |
| 6,890,295 | B2 | 5/2005 | Michels et al. |
| 6,939,296 | B2 | 9/2005 | Ewers et al. |
| 6,966,906 | B2 | 11/2005 | Brown |
| 7,440,661 | B2 | 10/2008 | Kobayashi |
| 7,485,092 | B1 | 2/2009 | Stewart et al. |
| 7,520,876 | B2 | 4/2009 | Ressemann et al. |
| 7,645,232 | B2 | 1/2010 | Shluzas |
| 7,837,612 | B2 | 11/2010 | Gill et al. |
| 7,846,107 | B2 | 12/2010 | Hoffman et al. |
| 9,101,390 | B2 | 8/2015 | Singh et al. |
| 10,736,659 | B2 | 8/2020 | Rokde |
| 2001/0044570 | A1 | 11/2001 | Ouchi et al. |
| 2002/0035311 | A1 | 3/2002 | Duchi |
| 2004/0102804 | A1 | 5/2004 | Chin |
| 2004/0138529 | A1 | 7/2004 | Wiltshire et al. |
| 2004/0204734 | A1 | 10/2004 | Wagner et al. |
| 2005/0033237 | A1 | 2/2005 | Fentress et al. |
| 2005/0065543 | A1 | 3/2005 | Kahle et al. |
| 2005/0107816 | A1 | 5/2005 | Pingleton et al. |
| 2005/0137459 | A1 | 6/2005 | Chin et al. |
| 2005/0149096 | A1 | 7/2005 | Hilal et al. |
| 2005/0272975 | A1 | 12/2005 | McWeeney et al. |
| 2005/0288622 | A1 | 12/2005 | Albrecht et al. |
| 2006/0047284 | A1 | 3/2006 | Gresham |
| 2006/0161049 | A1 | 7/2006 | Beane et al. |
| 2006/0224174 | A1 | 10/2006 | Smith et al. |
| 2006/0247500 | A1 | 11/2006 | Voegele et al. |
| 2006/0247516 | A1 | 11/2006 | Hess et al. |
| 2006/0247586 | A1 | 11/2006 | Voegele et al. |
| 2006/0247673 | A1 | 11/2006 | Voegele et al. |
| 2006/0247678 | A1 | 11/2006 | Weisenburgh et al. |
| 2006/0270911 | A1 | 11/2006 | Voegele et al. |
| 2007/0129719 | A1 | 6/2007 | Kendale et al. |
| 2007/0260121 | A1 | 11/2007 | Bakos et al. |
| 2007/0270653 | A1* | 11/2007 | Vayser ............... A61B 1/00135 600/182 |
| 2008/0086160 | A1 | 4/2008 | Mastri et al. |
| 2008/0194973 | A1 | 8/2008 | Imam |
| 2008/0300617 | A1 | 12/2008 | Smith |
| 2009/0023986 | A1 | 1/2009 | Stewart et al. |
| 2009/0036744 | A1 | 2/2009 | Vayser |
| 2010/0016664 | A1 | 1/2010 | Viola |
| 2010/0063450 | A1 | 3/2010 | Smith et al. |
| 2010/0063452 | A1 | 3/2010 | Edelman et al. |
| 2010/0318112 | A1 | 12/2010 | Smith |
| 2011/0118553 | A1 | 5/2011 | Stopek |
| 2011/0257478 | A1 | 10/2011 | Kleiner |
| 2011/0313242 | A1 | 12/2011 | Surti |
| 2012/0265022 | A1 | 10/2012 | Menn |
| 2012/0289816 | A1 | 11/2012 | Mark et al. |
| 2014/0249371 | A1 | 9/2014 | Fischvogt |

FOREIGN PATENT DOCUMENTS

| | | |
|---|---|---|
| EP | 0401432 A1 | 12/1990 |
| EP | 0664992 A1 | 8/1995 |
| EP | 2000099 A2 | 12/2008 |
| JP | H08266548 A | 10/1996 |
| JP | 2005503230 A | 2/2005 |
| JP | 2006289083 A | 10/2006 |
| JP | 2007516737 A | 6/2007 |
| JP | 2008504886 A | 2/2008 |
| JP | 2008296027 A | 12/2008 |
| JP | 2011125709 A | 6/2011 |
| WO | 2004075930 A2 | 9/2004 |
| WO | 2006110733 A2 | 10/2006 |
| WO | 2008077080 A2 | 6/2008 |
| WO | 2008103400 A2 | 8/2008 |

OTHER PUBLICATIONS

Supplementary European Search Report issued in corresponding EP application No. 12840970.3 dated Jul. 8, 2015.
Examination Report issued in corresponding Australian Patent Application No. 2012326322 dated May 17, 2016.
Japanese Office Action dated Aug. 1, 2016 in corresponding Japanese Patent Application No. 2014-537147, together with English translation, 12 pages.
Japanese Notice of Allowance dated Dec. 7, 2016 in corresponding Japanese Patent Application No. 2014-537147, together with English summary, 5 pages.
Examination Report No. 2 in corresponding Australian Application No. 2012326322, dated Feb. 9, 2017, 4 pages.
Australian Examination Report issued in corresponding Australian Patent Application No. 2017216514 dated Nov. 30, 2017.
International Search Report for PCT/US12/60392, dated Mar. 21, 2013 (3 pages).
European Search Report dated Feb. 17, 2020, corresponding to European Application No. 19204512.8; 6 pages.

* cited by examiner

OPTICAL TROCAR ASSEMBLY

CROSS-REFERENCE TO RELATED APPLICATION

This application is a continuation application of U.S. patent application Ser. No. 16/167,625, filed on Oct. 23, 2018, the entire contents of which being incorporate by reference herein.

BACKGROUND

Technical Field

The present disclosure relates to a trocar assembly for use in minimally invasive surgical procedures, such as endoscopic or laparoscopic type procedures.

Background of Related Art

Minimally invasive procedures are continually increasing in number and variation. Forming a relatively small diameter temporary pathway to the surgical site is a key feature of most minimally invasive surgical procedures. The most common method of providing such a pathway is by inserting a trocar assembly through the skin. Trocar assemblies with seal mechanisms may be utilized to provide the necessary pathway to the surgical site while minimizing leakage of insufflation gases.

Trocar assemblies typically include an obturator and a cannula. The cannula, having the obturator inserted therethrough, is directed through the skin to access a body cavity. Once the body cavity is accessed and subsequent to removal of the obturator from the cannula, laparoscopic or arthroscopic surgery and endoscopic procedures may be performed. With the cannula providing access to the body cavity, a surgical instrument (e.g., an endoscope or a laparoscope) may be guided into the body cavity through the cannula.

SUMMARY

In an aspect of the present disclosure, a cannula assembly configured to receive a surgical instrument therethrough is provided. The cannula assembly includes an elongated body portion, a housing coupled to a proximal end portion of the elongated body portion, and an annular-shaped light member. The housing defines a longitudinally-extending channel therethrough dimensioned for passage of a surgical instrument. The light member is disposed about the channel.

In some aspects, the housing may have an upper surface defining an aperture in communication with the channel.

In some aspects, the light member may be disposed adjacent the aperture.

In some aspects, the upper surface of the housing may be clear to provide visual access of the light member.

In some aspects, the housing may be detachable from the proximal end portion of the elongated body portion to allow for the selective coupling of an obturator assembly to the proximal end portion of the elongate body portion.

In some aspects, the cannula assembly may further include a light pipe extending through the elongated body portion and configured to transfer light emitted from the light member to a distal end portion of the elongated body portion.

In some aspects, the light pipe may have a proximal end portion disposed adjacent the light member, and a distal end portion disposed adjacent the distal end portion of the elongated body portion.

In some aspects, the cannula assembly may further include a battery electrically coupled to the light member for powering the light member.

In some aspects, the light member may include a light-emitting-diode (LED).

In some aspects, the light member may be disposed within the housing.

Further scope of applicability of the present disclosure will become apparent from the detailed description given hereinafter. However, it should be understood that the detailed description and specific examples, while indicating embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

Figure 1:
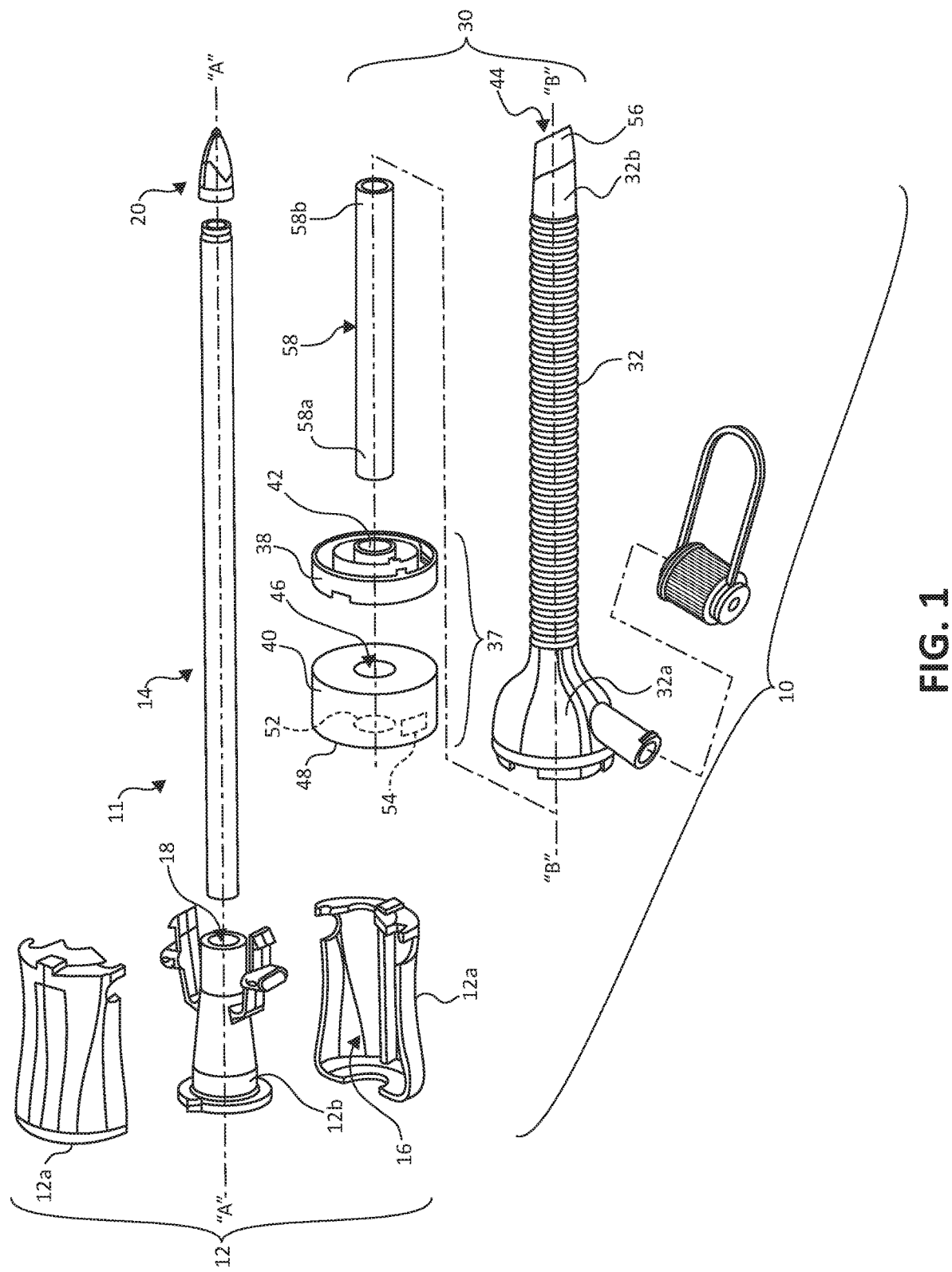
FIG. 1 is a perspective view, with parts separated, of an exemplary embodiment of a trocar assembly including a cannula assembly and an obturator assembly.

The figures depict embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION

Embodiments of the present disclosure are described hereinbelow with reference to the accompanying drawings. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

For the purposes of promoting an understanding of the principles of the present disclosure, reference will now be made to the exemplary embodiments illustrated in the drawings, and specific language will be used to describe the same. It will nevertheless be understood that no limitation of the scope of the present disclosure is thereby intended. Any alterations and further modifications of the inventive features illustrated herein, and any additional applications of the principles of the present disclosure as illustrated herein, which would occur to one skilled in the relevant art and having possession of this disclosure, are to be considered within the scope of the present disclosure.

The present disclosure, in accordance with various example embodiments thereof, relates to an optical trocar system that provides access to a body cavity through an anatomical, e.g., abdominal, wall. It should be noted that, for the purposes of this description, the term optical trocar system may be used herein synonymously with the term visual obturator system. Advantageously, the optical trocar system of the present disclosure, in accordance with various embodiments thereof, includes a cannula assembly having a ring of LEDs disposed near an opening of an elongated body portion of the cannula assembly. The ring of LEDs assists a clinician in guiding the surgical instrument into the opening of the elongated body portion. The cannula assembly may further include a light pipe extending from the ring of LEDs to a distal end portion of the elongated body portion to carry light from the ring of LEDs to the distal end portion.

Figure 2:
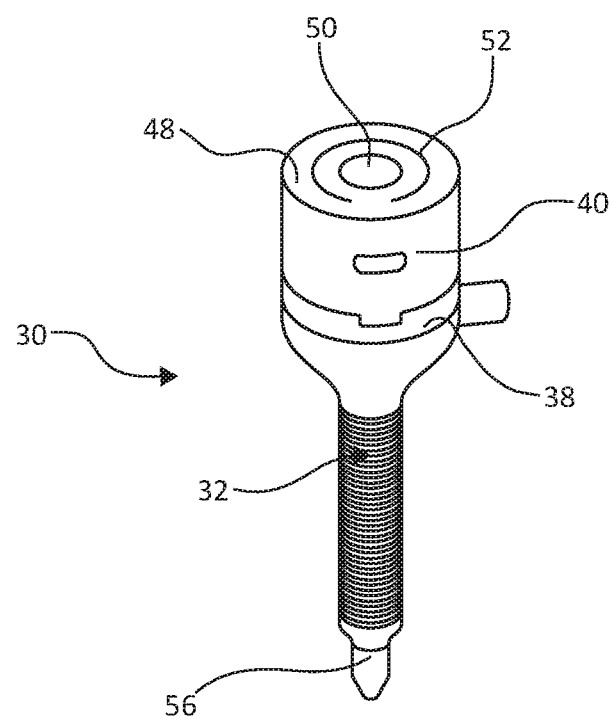
FIG. 2 is a top, perspective view of the cannula assembly of FIG. 1.

Referring now to FIGS. 1 and 2, there is illustrated an optical trocar, e.g., visual obturator, system or assembly 10 in accordance with an embodiment of the present disclosure. The visual obturator system 10 is intended for separating tissue planes in an endoscopic, e.g., laparoscopic, surgical procedure, and, is particularly suitable for the blunt dissection of the abdominal lining during a surgical procedure. The visual obturator system 10 is adapted to receive an endoscope to permit viewing of tissue during the insertion and advancement of the visual obturator system 10 toward the operative site. The visual obturator system 10 is also adapted to receive any other suitable surgical instrument for performing a surgical procedure at the operative site.

For a detailed description of an exemplary visual obturator system, reference may be made to U.S. Pat. No. 10,022,149, filed on Mar. 23, 2015, the entire contents of which are incorporated by reference herein.

In accordance with the embodiment shown, the visual obturator system 10 generally includes an obturator assembly 11 and a cannula assembly 30 which at least partially receives the obturator assembly 11. The obturator assembly 11 of the visual obturator system 10 includes an obturator housing assembly 12 selectively connectable with an elongated obturator shaft 14 of the obturator assembly 11. The obturator housing assembly 12 includes an outer housing 12a, and an inner housing 12b supported on a proximal end portion of the elongated obturator shaft 14. The outer housing 12a may be constructed from two half-sections joined to one another. The outer housing 12a defines a cavity 16 therein in which the inner housing 12b is situated. The inner housing 12b defines a central passageway 18 extending longitudinally therethrough that is coaxial with a longitudinal axis "A-A" defined by the elongated obturator shaft 14. The elongated obturator shaft 14 extends distally from the obturator housing assembly 12 and may be rigid, e.g., metal. The elongated obturator shaft 14 may be attached, e.g., by over molding thereto, at its proximal end portion to the obturator housing assembly 12 and at its distal end portion to an optical member 20.

The cannula assembly 30 of the visual obturator system 10 includes an elongated body portion 32 defining a longitudinal axis "B-B," and a housing assembly 37 detachably connected to a proximal end portion 32a of the elongated body portion 32. The elongated body portion 32 may be fabricated from a polymeric material, e.g., polycarbonate, and may be transparent, or at least semi-transparent, to permit passage of light rays. The elongated body portion 32 permits the passage of light rays to enable viewing of tissue during a surgical procedure. In other embodiments, the elongated body portion 32 may be opaque.

The cannula housing assembly 37 of the cannula assembly 30 and the obturator housing assembly 12 of the obturator assembly 11 may be selectively interchangeably connected to the proximal end portion 32a of the elongated body portion 32. For example, since the obturator assembly 11 is configured to receive a viewing instrument (e.g., an endoscope), the obturator housing assembly 12 may be connected to the proximal end portion 32a of the elongated body portion 32 during advancement of the optical trocar assembly 10 toward the operative site. During the performance of a surgical procedure using a surgical instrument (e.g., a suture passer), the cannula housing assembly 37 may be connected to the proximal end portion 32a of the elongated body portion 32.

The cannula housing assembly 37 is configured to provide a seal about a surgical instrument (e.g., a suture passer) inserted therethrough and prevent gasses from exiting the proximal end of the cannula assembly 30 in the absence of a surgical instrument positioned therein. The housing assembly 37 includes a cover 38 coupled to the proximal end portion 32a of the elongated body portion 32, and a housing 40 coupled to the cover 38. In embodiments, the housing 40 and cover 38 may be an integral unit. The cover 38 defines a central channel 42 therethrough to permit passage of a surgical instrument into a channel 44 defined through the elongated body portion 32.

The housing 40 of the housing assembly 37 is detachably coupled to a proximal end portion of the cover 38. In embodiments, the housing 40 of the housing assembly 37 may be directly coupled to the proximal end portion 32a of the elongated body portion 32 instead of the cover 38. The housing 40 defines a longitudinally-extending channel 46 therethrough dimensioned for passage of a surgical instrument. Upon coupling the housing 40 to the cover 38, the channels 46, 42, 44 of the housing 40, the cover 38, and the elongated body portion 32, respectively, are coaxial. In embodiments, the housing assembly 37 may further include a seal member, such as, for example, a valve (not shown) to prevent fluids from exiting a proximal end of the cannula assembly 30.

The housing 40 has a clear upper surface 48 defining an aperture 50 in communication with the channel 46 to provide access into the channel 46. In embodiments, a valve (not shown) may be provided in the aperture 50 to permit entry of a surgical instrument into the channel 46 of the housing 40 while preventing fluids from exiting the channel 46 of the housing 40.

The housing assembly 37 further includes an annular-shaped light member 52 and a battery 54 electrically coupled to one another and disposed within the housing 40. In embodiments, the light member 52 and/or the battery 54 may be disposed outside of the housing 40. The light member 52 may include a plurality of lights, such as, for example, light-emitting-diodes (LEDs") arranged in a ring to at least partially surround the aperture 50 in the upper surface 48 of the housing 40. In other embodiments, the light member 52 may include one or more incandescent lights or fluorescent lights arranged in a ring. The light member 52 may be disposed on the clear upper surface 48 of the housing 40 or any suitable location within the housing 40 while also surrounding the channel 46 of the housing 40. By positioning the light member 52 so it appears around the aperture 50, a clinician will have a visual indication of the location of the aperture 50 to assist in guiding a surgical instrument into the cannula assembly 30.

The cannula assembly 30 further includes a light pipe 58 extending through the elongated body portion 32 and configured to transfer light emitted from the light member 52 to the distal tip 56 of the elongated body portion 32. The light pipe 58 may be a flexible or rigid hollow tube fabricated from a material suitable for transmitting light, such as, for example, acrylic or polycarbonate. In other embodiments, the light pipe 58 may be an optical fiber or fibers. The light pipe 58 has a proximal end portion 58*a* disposed adjacent the light member 52, and a distal end portion 58*b* disposed adjacent the distal tip 56 of the elongated body portion 32. The proximal end portion 58*a* of the light pipe 58 extends through the housing assembly 37 and may receive the light member 52. The distal end portion 58*b* of the light pipe 58 terminates within the distal tip 56 of the elongated body portion 32. It is contemplated that the light pipe 58 may have markings or cuts (not shown) along a length thereof configured to emit a greater intensity of light than the remainder of the light pipe 58 to provide a visual indication of the depth of the cannula assembly 30 or the location of various segments of the cannula assembly 30.

The operation of the optical trocar system 10 and, specifically the cannula assembly 30, will now be described. The obturator shaft 14 of the obturator assembly 11 may be positioned through the elongated body portion 32 of the cannula assembly 30 and the obturator housing assembly 12 of the obturator assembly 11 may be connected to the proximal end portion 32*a* of the elongated body portion 32 of the cannula assembly 30. The assembled optical trocar system 10 is positioned within an initial incision and against targeted tissue, e.g., an abdominal lining. A viewing instrument, such as an endoscope (not shown), may be inserted through the obturator housing assembly 12 of the obturator assembly 11 to assist in guiding the distal tip 56 of the elongated body portion 32 to the operative site.

Upon positioning the distal tip 56 of the elongated body portion 32 at the operative site, the obturator assembly 11 may be detached from the proximal end portion 32*a* of the elongated body portion 32 and replaced with the housing assembly 37. With the housing assembly 37 attached to the proximal end portion 32*a* of the elongated body portion 32, a switch on the housing 40, such as, for example, a pull-tab (not shown), may be activated to transfer power from the battery 54 to the light member 52, thereby generating a ring of light about the aperture 50 in the housing 40. A clinician, using the ring of light generated by the light member 52 as a guide, may position a surgical instrument into the cannula assembly 30 via the aperture 50. The light pipe 58 directs the light from the light member 52 toward the distal tip 56 of the elongated body portion 32 to assist the clinician during the surgical procedure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. A cannula assembly configured to receive a surgical instrument therethrough, the cannula assembly comprising:
   an elongated body portion;
   a housing coupled to a proximal end portion of the elongated body portion, the housing defining a longitudinally-extending channel therethrough dimensioned for passage of the surgical instrument;
   a light pipe having a proximal end portion received within and attached to the housing, the light pipe extending distally from the housing and disposed in a lumen of the elongated body portion; and
   an annular-shaped light member at least partially encircling the channel.

2. The cannula assembly according to claim 1, wherein the light member is attached to the housing.

3. The cannula assembly according to claim 1, wherein the housing has an upper surface defining an aperture in communication with the channel, the light member being disposed adjacent the aperture.

4. The cannula assembly according to claim 3, wherein the upper surface of the housing is optically clear to provide visual access of the light member.

5. The cannula assembly according to claim 1, wherein the housing is detachable from the proximal end portion of the elongated body portion to allow for the selective coupling of an obturator assembly to the proximal end portion of the elongate body portion.

6. The cannula assembly according to claim 1, wherein the light pipe is configured to transfer light emitted from the light member to a distal end portion of the elongated body portion.

7. The cannula assembly according to claim 6, wherein the proximal end portion of the light pipe is disposed adjacent the light member, and the light pipe has a distal end portion disposed adjacent the distal end portion of the elongated body portion.

8. The cannula assembly according to claim 1, wherein the light member includes a plurality of light-emitting-diodes (LEDs).

9. The cannula assembly according to claim 1, wherein the light member is disposed within the housing.

10. The cannula assembly according to claim 1, wherein the proximal end portion of the light pipe has the light member received therein.

11. The cannula assembly according to claim 1, further comprising a cover intercoupling the proximal end portion of the elongated body portion and the housing.

12. The cannula assembly according to claim 11, wherein the housing is configured to be detachably coupled to the cover.

13. A visual obturator system comprising:
   an obturator assembly including:
     an obturator housing assembly; and
     an elongated obturator shaft extending distally from the obturator housing assembly, the elongated obturator shaft defining a longitudinally-extending channel dimensioned for passage of a viewing instrument; and
   a cannula assembly including:
     an elongated body portion;

a housing defining a longitudinally-extending channel therethrough dimensioned for passage of a surgical instrument; and an annular-shaped light member attached to the housing and disposed about the channel, wherein the obturator housing assembly of the obturator assembly and the housing of the cannula assembly are configured to selectively interchangeably connect to a proximal end portion of the elongated body portion.

14. The visual obturator system according to claim 13, wherein the cannula assembly further includes a cover configured to detachably couple to the proximal end portion of the elongated body portion, the housing being configured to be detachably coupled to the cover.

15. The visual obturator system according to claim 13, wherein the cannula assembly further includes a light pipe having a proximal end portion received within and attached to the housing, the light pipe extending distally from the housing and configured for receipt in the elongated body portion.

16. The visual obturator system according to claim 15, wherein the proximal end portion of the light pipe has the light member received therein.

17. The visual obturator system according to claim 13, wherein the housing has an upper surface defining an aperture in communication with the channel, the light member being disposed adjacent the aperture.

18. The visual obturator system according to claim 17, wherein the upper surface of the housing is optically clear to provide visual access of the light member.

19. The visual obturator system according to claim 13, wherein the light member is disposed within the housing.

20. A cannula assembly configured to receive a surgical instrument therethrough, the cannula assembly comprising:

an elongated body portion;

a housing coupled to a proximal end portion of the elongated body portion, the housing defining a longitudinally-extending channel therethrough dimensioned for passage of the surgical instrument, the housing detachable from the proximal end portion of the elongated body portion to allow for the selective coupling of an obturator assembly to the proximal end portion of the elongate body portion;

a light pipe having a proximal end portion received within and attached to the housing, the light pipe extending distally from the housing and configured for receipt in the elongated body portion; and an annular-shaped light member at least partially encircling the channel.

* * * * *